US006803577B2

(12) United States Patent
Edner et al.

(10) Patent No.: US 6,803,577 B2
(45) Date of Patent: Oct. 12, 2004

(54) QUANTITATIVE IMAGING OF GAS EMISSIONS UTILIZING OPTICAL TECHNIQUES

(75) Inventors: Hans Edner, Lund (SE); Jonas Sandsten, Lomma (SE); Sune Svanberg, Lund (SE)

(73) Assignee: Gas Optics Sweden AB, Lund (SE)

( * ) Notice: Subject to any disclaimer, the term of this patent is extended or adjusted under 35 U.S.C. 154(b) by 141 days.

(21) Appl. No.: 10/169,300

(22) PCT Filed: Dec. 28, 2000

(86) PCT No.: PCT/SE00/02686

§ 371 (c)(1),
(2), (4) Date: Jun. 27, 2002

(87) PCT Pub. No.: WO01/48459

PCT Pub. Date: Jul. 5, 2001

(65) Prior Publication Data

US 2003/0025081 A1 Feb. 6, 2003

(30) Foreign Application Priority Data

Dec. 28, 1999 (SE) .............................................. 9904836

(51) Int. Cl.[7] .............................................. G01N 21/35
(52) U.S. Cl. .............. 250/339.09; 250/330; 250/339.13
(58) Field of Search ........................ 250/339.09, 338.5, 250/339.04, 339.12, 339.13, 330

(56) References Cited

U.S. PATENT DOCUMENTS

| | | | | |
|---|---|---|---|---|
| 3,976,884 A | * | 8/1976 | Acton et al. ................. | 250/343 |
| 4,555,627 A | * | 11/1985 | McRae, Jr. ................... | 250/334 |
| 4,967,276 A | * | 10/1990 | Murakami et al. .......... | 348/164 |
| 5,210,702 A | * | 5/1993 | Bishop et al. ................ | 702/24 |
| 5,373,160 A | * | 12/1994 | Taylor ..................... | 250/338.5 |
| 5,656,813 A | * | 8/1997 | Moore et al. ............... | 250/330 |
| 6,690,472 B2 | * | 2/2004 | Kulp et al. .................. | 356/437 |

FOREIGN PATENT DOCUMENTS

DE 4324154 A1 7/1993

OTHER PUBLICATIONS

"Novel Remote Gas Monitoring and Imaging in the IR Spectral Region," H. Edner, J. Sandsten, Y. Saito, J. Smith, S. Svanberg and P. Weibring, *CLEO/Pacific Rim '99*, pp. 577–578.

"State–of–the–Art and Future Plans for IR Imaging of Gaseous Fugitive Emission," Sven–Ake Ljungberg, *International Conference on Thermal Sensing and Imaging Diagnostic Applications*, vol. 3056, Orlando, 1997.

"Remote Imaging of Controlled Gas Releases using Active and Passive Infrared Imaging Systems," Thomas J. Kulp, Peter E. Powers, and Randall Kennedy, *Proceedings of the Society of Photo–Optical Instrumentation Engineers*, vol. 3061, 1997.

* cited by examiner

*Primary Examiner*—Albert Gagliardi
(74) *Attorney, Agent, or Firm*—Boyle, Fredrickson, Newholm, Stein & Gratz, S.C.

(57) ABSTRACT

A method for quantitative imaging of gas emissions utilizing optical techniques combining gas correlation techniques with thermal background radiation or gas self-emission radiation is presented. A simultaneous recording of images with and without filtering through a gas-filled cell is utilized for the identification of a selected gas. A new calibration method provides the display of the integrated gas concentration spatially resolved in the generated final image. The procedure includes methods for a correct subtraction of the zero level, consisting of self-radiation from the dual-image camera device including the as correlation cell and electronic offset, and for the calculation of the specific absorption as a function of the difference temperature between the background and the gas emission.

25 Claims, 9 Drawing Sheets

QUANTITATIVE IMAGING OF GAS EMISSIONS UTILIZING OPTICAL TECHNIQUES

FIELD OF THE INVENTION

The present invention concerns quantitative imaging or gas emissions utilizing optical techniques. It is of great interest to be able to detect and quantify gas flows. Leakage of hydrocarbons from oil rigs, petrochemical industry, tank farms or natural gas pipelines constitute an economical loss, an environmental problem and a safety concern. Releases in connection with accidents involving transport vehicles or in industrial operations need to be controlled. Natural emissions of green-house gases from geophysical sources, e.g. volcanoes, geothermal plants or marshes or bogs need to be chartered. In the indoor environment it is important to be able to control the functioning of a ventilation system or an air extraction channel. It would be of great interest if the gas releases could be visualized and quantified in near real time, since the remedy actions in many cases need to be launched immediately. Gas imaging can be performed based on the selective absorption of optical radiation. If an artificial light source is used we talk about active techniques while the utilization of the background radiation is referred to as passive techniques. The infrared thermal background radiation is of special interest for passive imaging. In a non-limiting embodiment of the invention this radiation is used for quantitative imaging of flowing hydrocarbons.

BACKGROUND OF THE INVENTION

Molecular gases exhibit characteristic absorption lines in the visible and ultra-violet spectral region (electronic transitions) and in the infrared spectral region (rotational-vibrational transitions). The presence of gas in the atmosphere is manifested through absorption of a transmitted beam at specific wavelengths. The well-known DOAS (differential Absorption Optical Spectroscopy) technique as well as the Fourier-Transform Spectrometry principle utilizes light from a continuos light source, with the beam transmitted over an atmospheric path ending at the receiver. Alternatively, the sky radiation can be utilized, which is the case also when correlation techniques are used (COSPEC techniques with a mechanical mask arrangement in the image plane of the spectrometer, or gas correlation techniques with a gas cell intermittently introduced in the light pathway in front of the detector). Tuneable semiconductor lasers can also be utilized for absorption spectroscopy of molecular gases. Pulsed laser systems allow range-resolved monitoring of gas clouds utilizing differential absorption lidar (LIght Detection And Ranging).

The techniques mentioned above deal with measurements over given paths. However, imaging of the extension of a gas cloud is important in many cases. This can be achieved with imaging lidar techniques. A more simple approach is to utilize passive techniques. This has been achieved in the infrared spectral region utilizing a "heat camera", which has been equipped with a band pass filter for the absorption region of the particular gas. If a sufficient amount of gas is present it can be visualized with a lower intensity than the surrounding. The fact that many gases, such as hydrocarbons, absorb in the same wavelength range, constitutes a problem. The gas correlation technique then provides an automatic discrimination between the gases as recently has been reported. Two images are then recorded, a direct one and one through a gas cell, containing the particular kind of gas to be imaged, in an optically thick concentration. The gas completely blocks the gas of interest and provides a reference image. However, the direct image is influenced by the specific gas absorption. By subtraction or division of the images the gas is enhanced, and the surrounding areas are eliminated. Other gases with absorption lines not matching the gas filter are also eliminated by this image processing. Until recently, gas correlation techniques needed to utilize an artificially heated background surface in order to reach a sufficient level of thermal radiation.

BRIEF DESCRIPTIONS OF THE DRAWINGS

Figure 8:
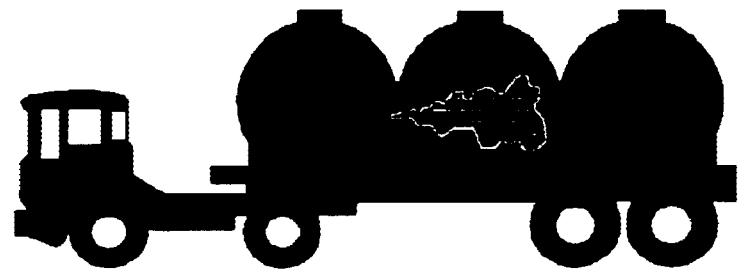
Figure 8:
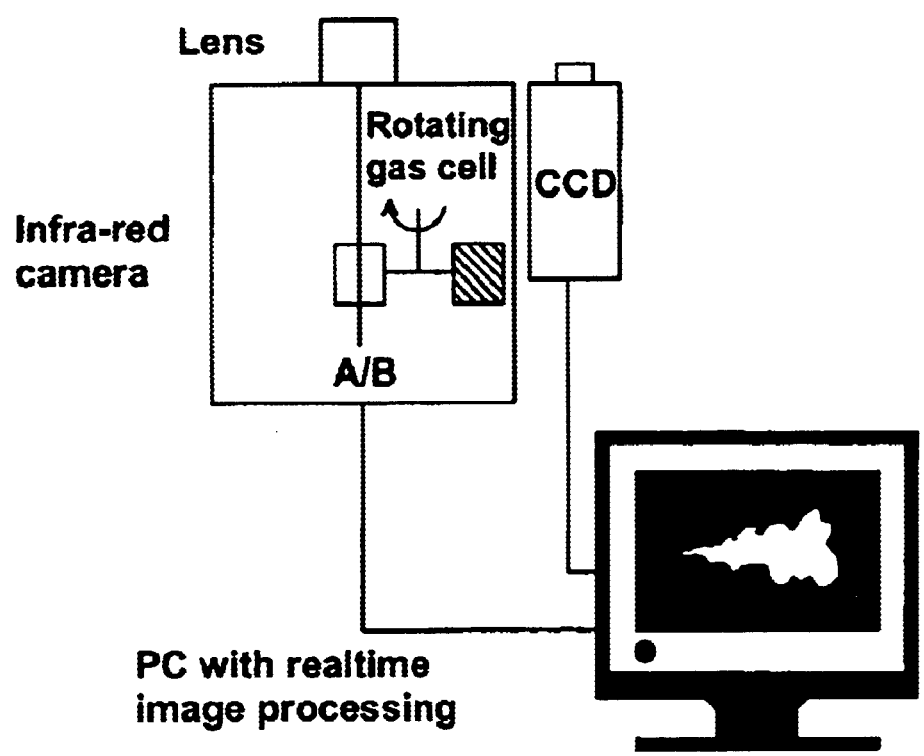

FIG. 8. shows a scenario for quantified gas measurements utilizing the gas correlation technique with a rotating chopper mounted gas cell inside the infra-red camera. The images are sequentially captured by a single detector.

Figure 9:
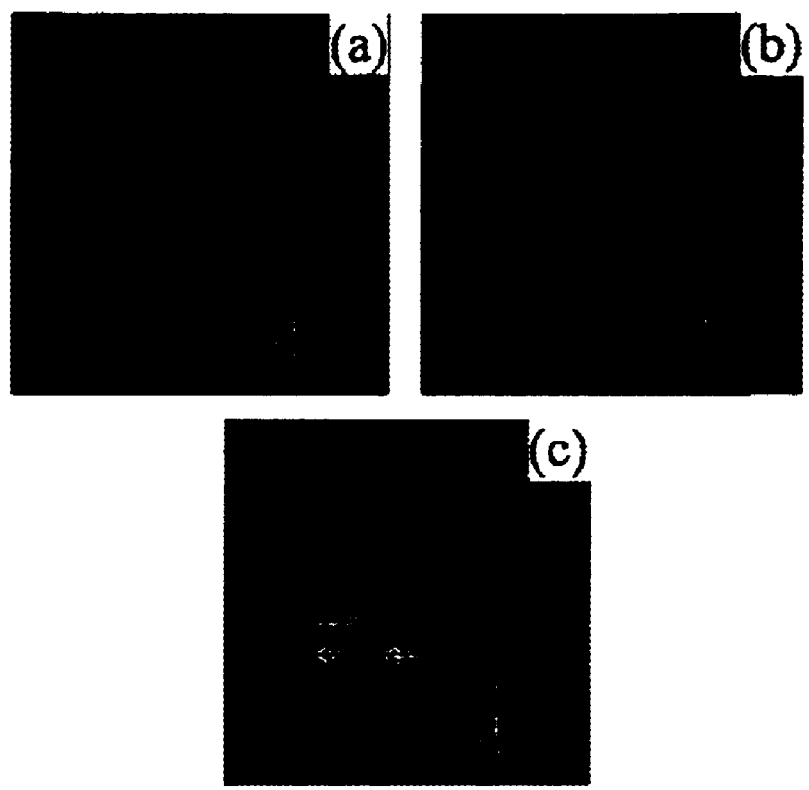

FIG. 9.(a) shows a gas-correlated ethene image at time $T_0$, (b) shows a gas-correlated ethene image at a later time $T_1$. (c) shows a wind vector map derived by cross-correlating the gas-correlated images at time $T_0$ and $T_1$. The resolution of the vector map is determined by the size of the small cross-correlation matrixes.

DESCRIPTION OF THE INVENTION

Figure 1:
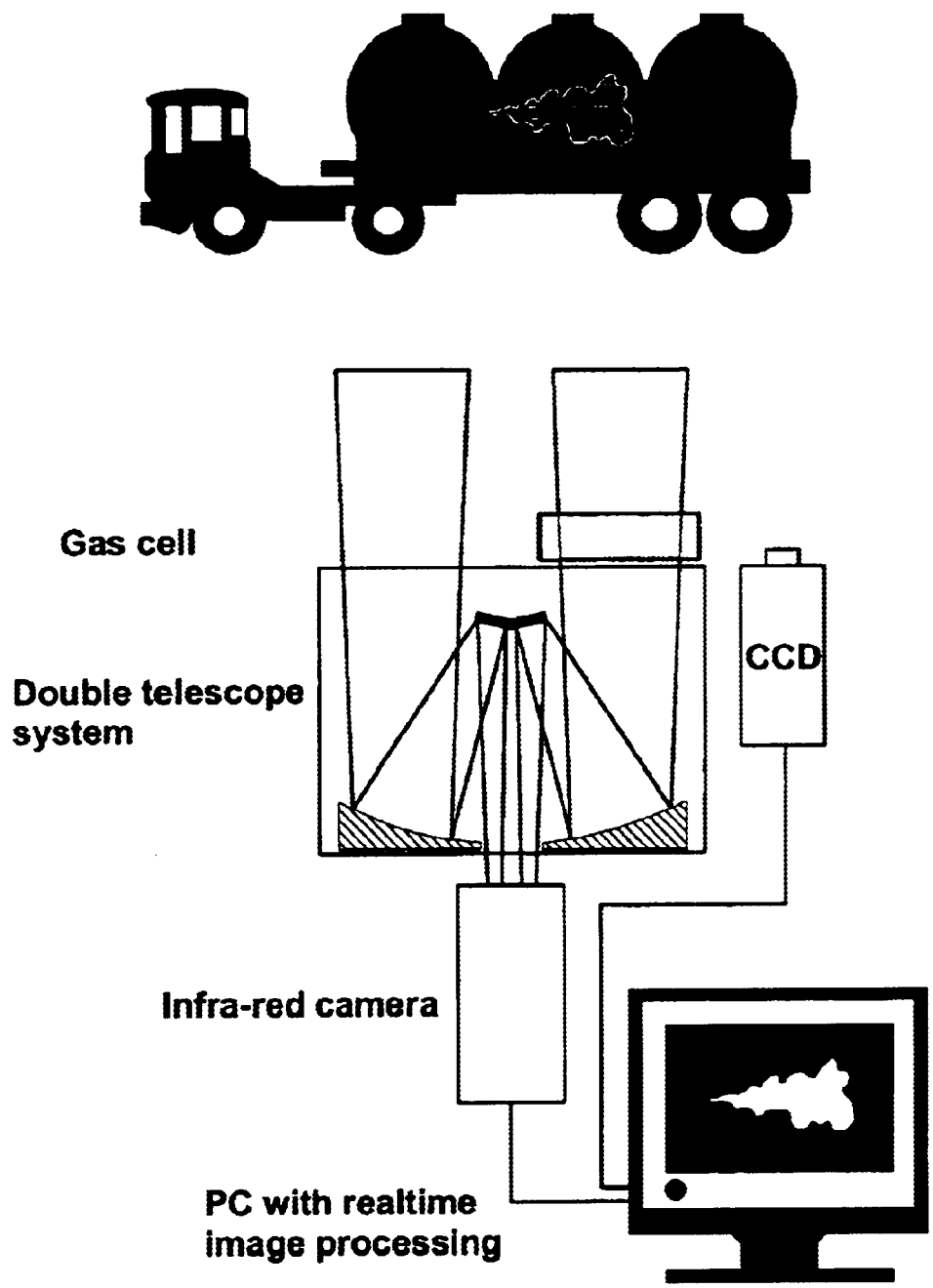
FIG. 1 shows a scenario for quantified gas measurements utilizing the gas correlation technique with the double telescope system.
Figure 2:
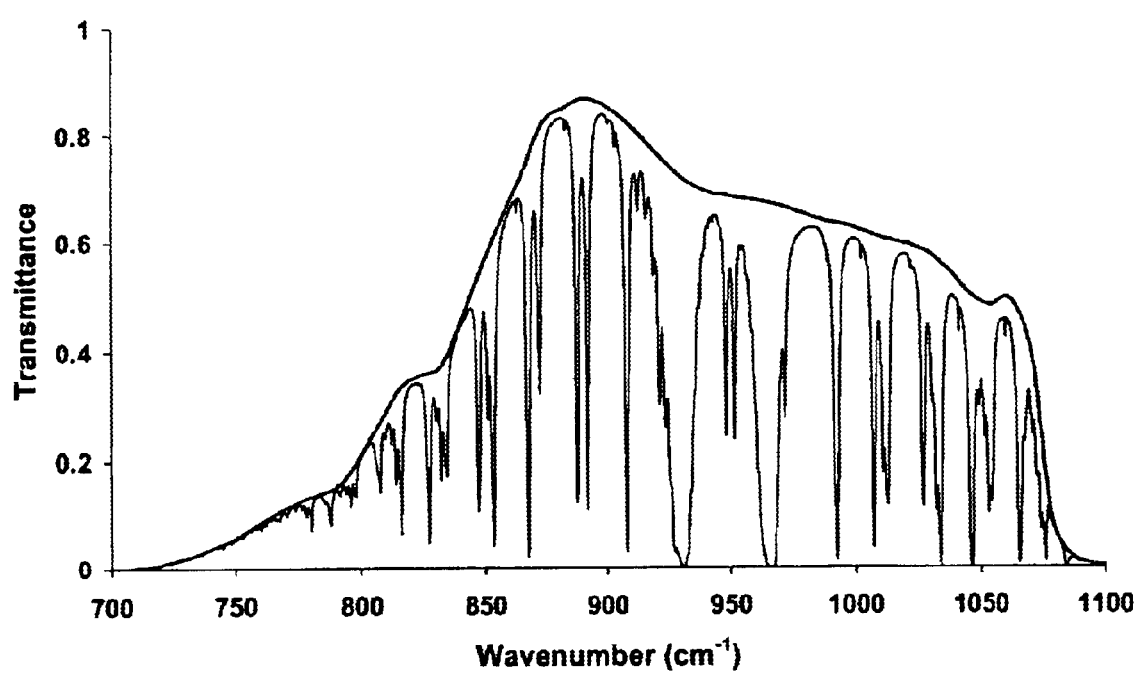
FIG. 2 shows an example of a gas absorption profile for ammonia, corresponding to an integrated gas concentration of 4000 ppm×meter.
Figure 3:
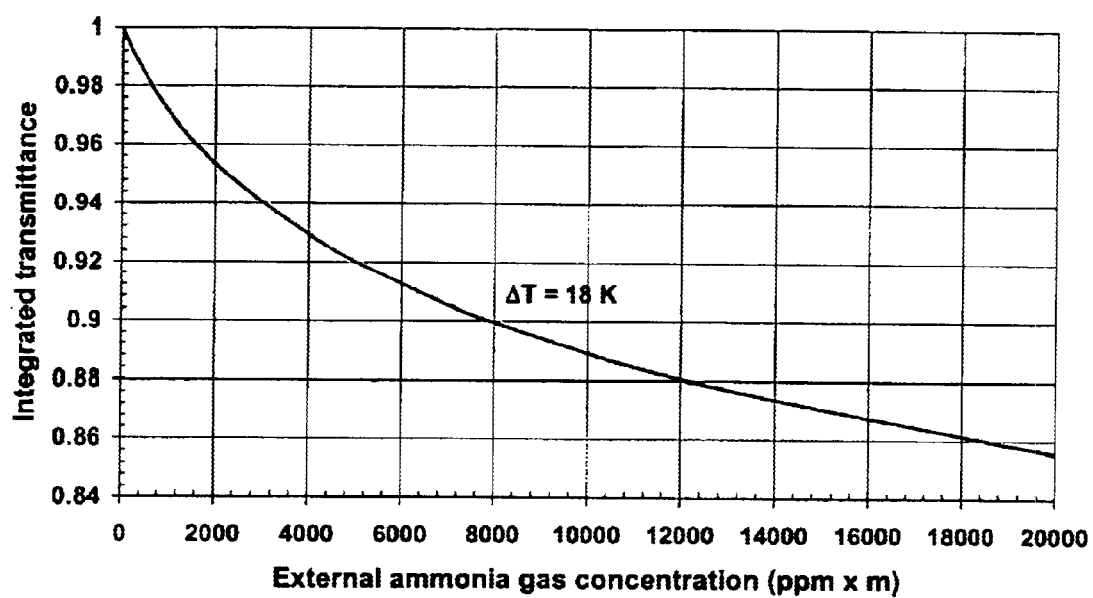
FIG. 3 shows a diagram displaying the sensitivity for external gas (in ppm×meter) when there is a temperature difference of 18 K between the background and the absorbing gas.
Figure 4:
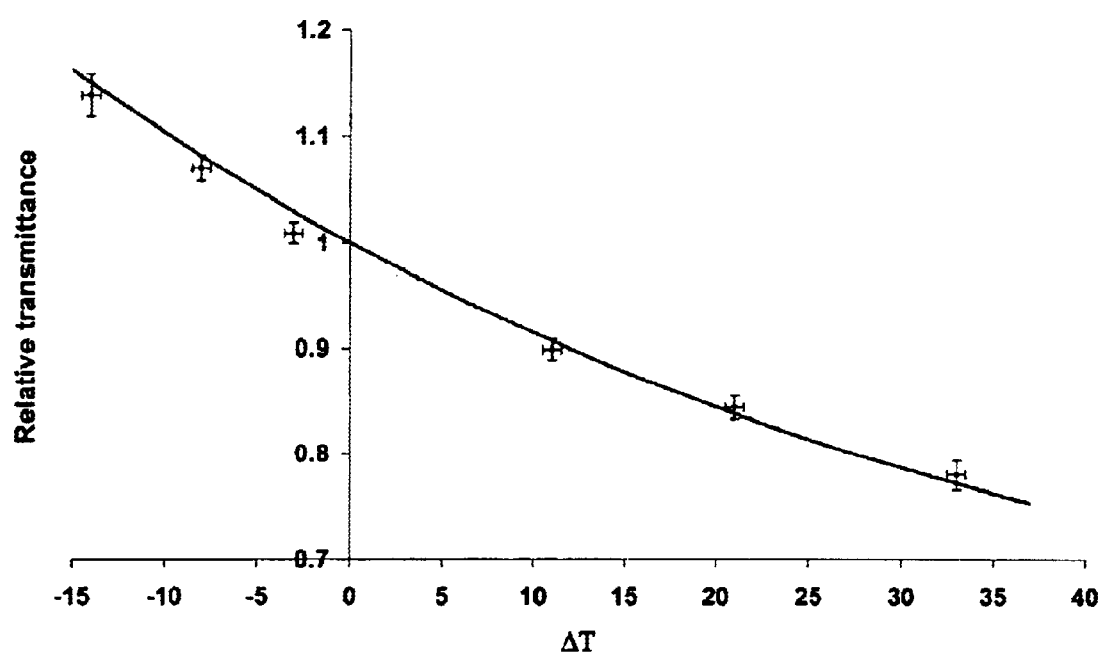
FIG. 4 shows a diagram displaying the theoretically calculated and experimentally established calibration curve for absolute gas concentration determinations.
Figure 5:
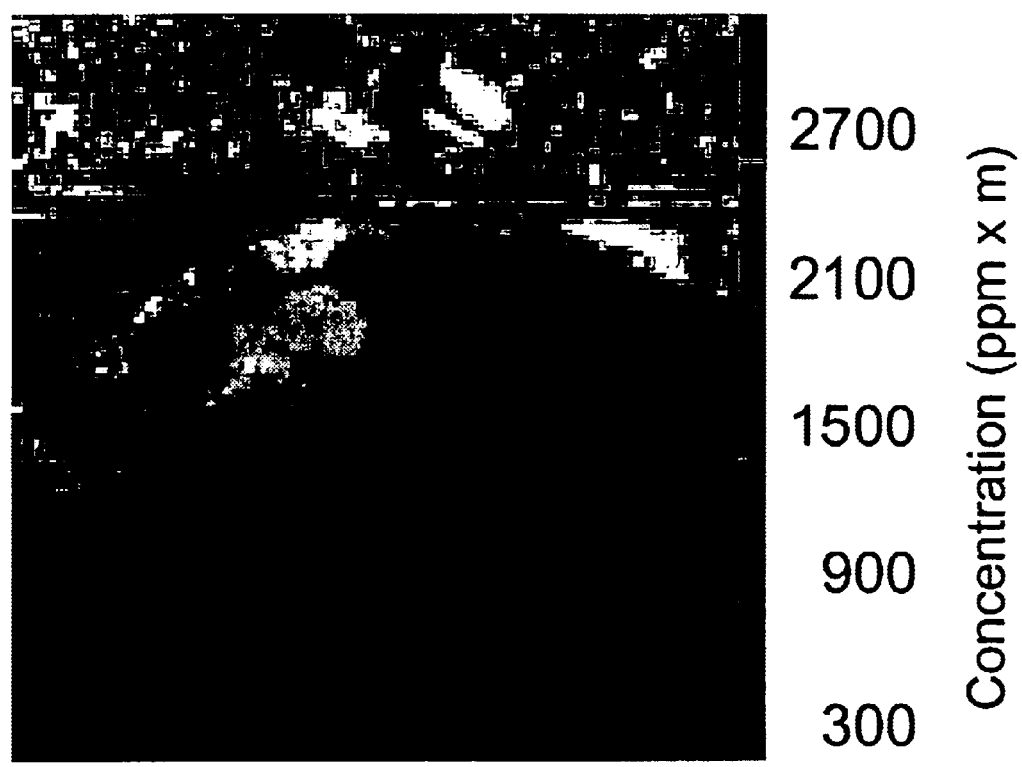
FIG. 5 shows an example of a concentration calibrated gas correlation image of escaping ammonia gas from a leaking tanker, recorded utilizing only natural background radiation and being part of a picture sequence with image updating 15 times per second.
Figure 6:
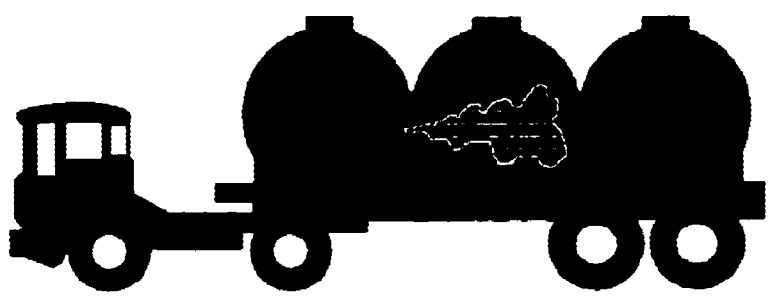
FIG. 6 shows a scenario for quantified gas measurements utilizing the gas correlation technique with two infrared cameras with the gas cell and lens mounted together on one of the cameras.
Figure 6:
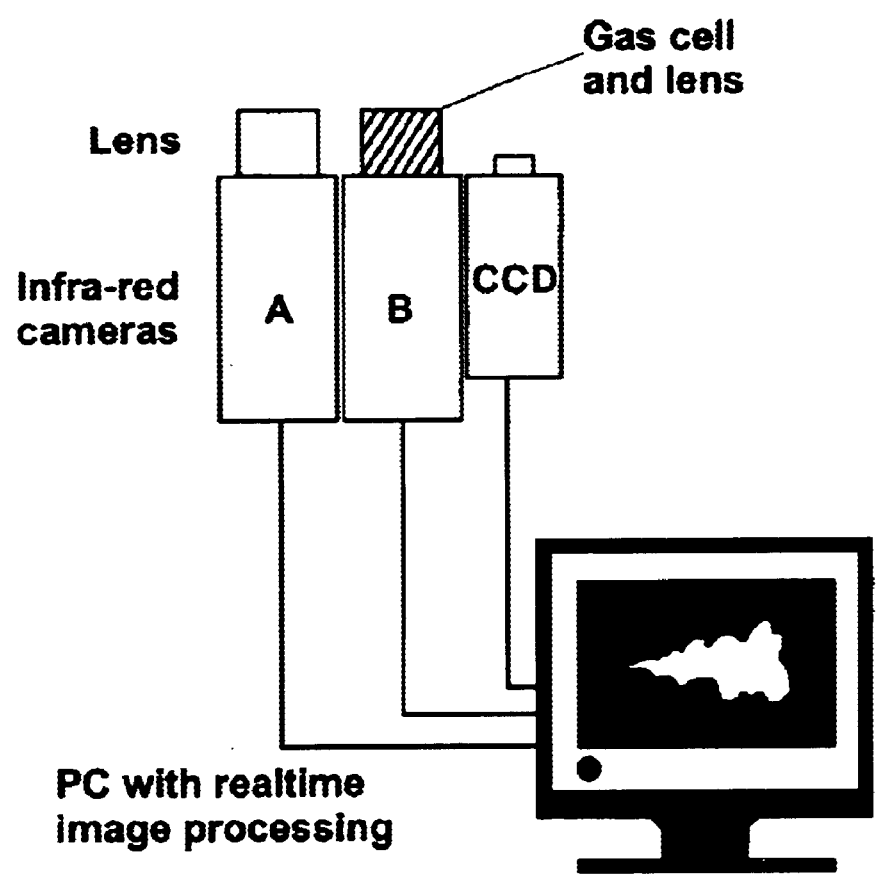

The present invention concerns important extensions of the gas correlation imaging concept. They particularly concern the possibility to quickly make quantitative determinations of gas concentrations and flows. The most important aspect of the present invention is that a new calibration method is brought forward for allowing the determination of the integrated concentration in a gas release. A scenario for measurements with the gas correlation method is given in FIG. 1. Emanating gas from a leaking tanker is monitored with a double telescope system, where one optical channel passes a gas correlation cell and where the two images are placed side by side in the image plane of a sensitive infrared camera. FIG. 2 shows an absorption spectrum for ammonia gas normalized to an experimental transmission profile for the optical system. If the gas cloud has a lower temperature than the background it shows up in the direct image with a weaker intensity; whereas it cannot be observed in the gas correlation channel, where the cell gas-has a stronger absorption. FIG. 3 shows the integrated transmission within the spectral profile considered, as a function of the integrated concentration of the gas, expressed in ppm×m (parts per million×meter). Here the actual temperature difference between the background and the gas (in this case 18 K) has been taken into consideration. FIG. 4 shows the relative transmittance which is obtained through an ammonia gas with an integrated concentration of 20000 ppm×m as a function of the temperature difference (experimental and theoretical (full line) data). From this diagram the influence of the temperature difference on the output signal can be determined (i.e., the sensitivity of the system). A relative transmittance higher than one corresponds to a gas self-emission radiation larger than the background radiation (i.e. the gas temperature is higher than the, background temperature). Finally, FIG. 5 shows an ammonia release gas correlation image, calculated for concentration.

More specifically, the gas correlation image processing and calibration is described by the following steps:

Two images, A and B are stored using a dual-image infrared camera device adapted to a selected wavelength region where the gas absorption or emission spectrum is present.

A—is the infrared scene recorded in one of the images (direct image).

B—is the same scene recorded with the infrared light passing a gas correlation cell.

The background temperature is recorded with the normal infrared camera routines in image A.

The relevant zero images $A_0$ and $B_0$, consisting of self-radiation from the dual-image camera device including the gas correlation cell and electronic offset, are subtracted from A and B, respectively. The individual zero level in each pixel of the images has before the gas measurement been determined by recording a black body radiator at different temperatures and plotting the pixel intensity obtained versus a theoretically calculated intensity. The axis intercept of a straight line, which is fitted to the data, provides the zero level.

The images are digitally overlapped within a field of interest containing the gas release, and the continuing image processing is constrained to this field.

A gas correlation image, $G=(A-A_0)/(B-B_0)$, is calculated

The concentration level in each pixel of image G is calculated using a diagram such as FIG. 3 showing the integrated transmission within the chosen spectral profile as a function of the integrated concentration of the gas expressed in ppm×meter for the particular gas, temperature difference and absolute temperatures.

Finally, the resulting gas concentration image is color-coded and superimposed on a visible image C of the scene and the result is displayed, generally with a high update frequency. In a measurement the infrared camera detector integration time, spatial/temporal filtering, and concentration threshold is adapted to the measured gas concentration level and dynamics at a rate allowing concentration calibrated images to be shown as movies.

Further aspects of the present invention are greatly improved optical arrangements compared to those of earlier descriptions Off-axis parabolas are used eliminating disturbing image vignetting and providing sharp images; plane and angled mirrors are utilized instead of a convex mirror in a Cassegrain-like telescope construction, providing elimination of the reflected self-radiation of the camera back into its detector.

Figure 7:
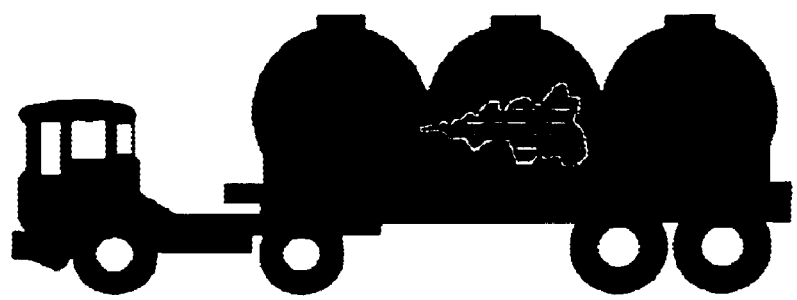
FIG. 7 shows a scenerio for quantified gas measurements utilizing the gas correlation technique with a beamsplitter inside the infra-red camera. The gas cell is situated in front of detector B.
Figure 7:
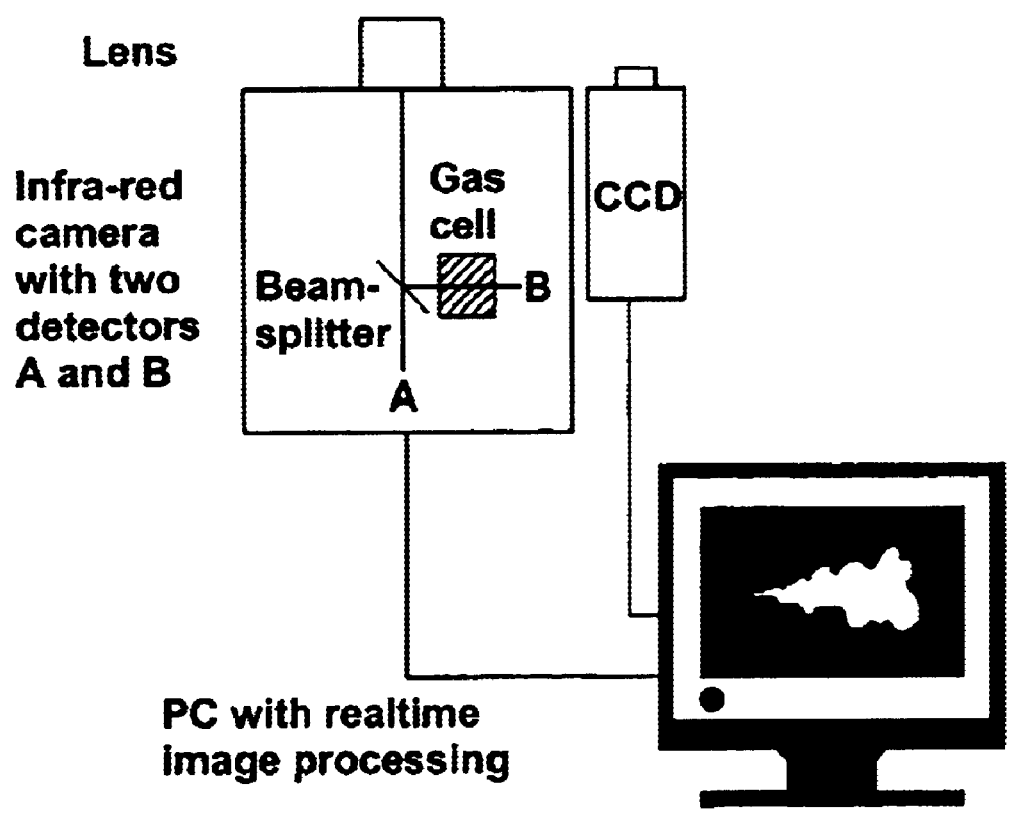

Alternatively, the two images A and B can be produced by two infra-red cameras mounted together, as shown in 6, or with a single camera width a beamsplitting unit and a gas correlation cell in front of one of two detectors inside the camera as seen in FIG. 7. Another solution is to use a single detector camera with the gas correlation cell mounted on a chopper in front of the detector, for sequential capturing of the images A and B, as shown in FIG. 8.

The utilization of a Quantum Well Infrared Photon (QWIP) detector with tailored sensitivity in a selected narrow wavelength region around the gas absorption/emission spectral features is especially suited for gas correlation imaging. A micro-bolometer camera spectrally tuned to the gas absorption/emission spectrum with the aid of antireflection coating and interference filters is an alternative.

With a calibrated gas concentration movie the flux can be deduced by combining the gas concentration image with the gas flow velocity, calculated through correlation of the displacement of the gas cloud in temporally separated images. A wind vector map is derived by cross-correlating a small matrix in an image at time To with a corresponding small matrix in an image at a later time, $T_1$. The size of the small matrixes are chosen by maximizing the cross-correlation product. By creating and moving the cross-correlation matrixes over the complete images a resulting time-correlated wind vector map can be produced. The resulting wind vector map merged with the image at time $T_0$ is shown in FIG. 9.

What is claimed is:

1. A method for imaging of gas distributions utilizing optical techniques, comprising: the use of gas correlation techniques for spectral identification of substances and cancellation of spatially varying background temperatures and emissivities;

the utilization of absorption of natural thermal background radiation or self-emission spectrum due to a selected gas (passive recording technique);

and wherein two images, A and B are stored using a dual-image infrared camera device adapted to a selected wavelength region where the gas absorption or emission spectrum is present;

A—is the infrared scene recorded in one of the images (direct image);

B—is the same scene recorded with the infrared light passing a gas correlation cell;

characterized by a calibration procedure as follows:

the background temperature is recorded using the information contained in image A;

the relevant zero images $A_0$ and $B_0$, consisting of self-radiation from the dual-image camera device including the gas correlation cell and electronic offset, are subtracted from A and B, respectively, wherein the individual zero level in each pixel of the images has been determined before the gas measurement by recording a black body radiator at different temperatures and plotting the pixel intensity obtained versus a theoretically calculated intensity, and the axis intercept of a straight line, which is fitted to the data, provides the zero level;

the images are digitally overlapped within a field of interest containing the gas release, and the continuing image processing is constrained to this field;

a gas correlation image, $G=(A-A_0)/(B-B_o)$, is calculated;

the concentration level in each pixel of image G is calculated using a diagram showing the integrated transmission within the chosen spectral profile as a function of the integrated concentration of the gas expressed in ppm×meter for the particular gas, temperature difference between the background temperature and the gas emission temperature, and absolute temperatures; and finally, the resulting gas concentration image is superimposed on a visible image C of the scene and the result is displayed.

2. A method as claimed in claim 1, characterized in that the resulting gas concentration image is colour-coded.

3. A method as claimed in claim 1 or 2, characterized by the adaption of the infrared camera detector integration time, spatial/temporal filtering, and concentration threshold to the measured gas concentration level and dynamics at a rate allowing concentration calibrated images to be shown as movies.

4. A method as claimed in claim 1 or 2, characterized by a determination of the gas flux by combining the gas, concentration image with the gas flow velocity, calculated through correlation of the displacement of the gas cloud in temporally separated images.

5. A method as claimed in claim 1 or 2, characterized of the utilization of a reflector double telescope with off-axis parabolas for simultaneous capturing of the images A and B. The visible image C is simultaneously captured with a camera mounted in close proximity to the telescope.

6. A method as claimed in claim 5, characterized by the use of plane and angled secondary telescope mirrors designed to avoid the self-radiation of the camera to be reflected back into the camera detector.

7. A method as claimed in claim 1 or 2, characterized by the use of two infrared cameras mounted together for simultaneous capturing of the images A and B. The visible image C is simultaneously captured with a camera mounted in close proximity to the infrared cameras.

8. A method as claimed in claim 1 or 2, characterized by the use of an infrared camera with two detectors capturing images A and B with the aid of a beam-splitter and gas correlation cell inside the camera. The visible image C is simultaneously captured with a camera mounted in close proximity to the infrared camera.

9. A method as claimed in claim 1 or 2, characterized by the use of an infrared camera with one detector sequentially capturing images A and B by the use of a chopper switching the gas correlation cell in and out in front of the detector. The visible image C is simultaneously captured with a camera mounted in close proximity to the infrared camera.

10. A device for imaging of gas distributions utilizing optical techniques, comprising:

a dual-image infrared camera device, for storing two images, A and B and adapted to a selected wavelength region where the gas absorption or emission spectrum is present wherein:

A—is the infrared scene recorded in one of the images (direct image);

B—is the same scene recorded with the infrared light passing a gas correlation cell;

characterized in that the camera device includes means for calibration comprising:

means for recording the background temperature using the information contained in image A;

means for determining and storing the relevant zero images $A_0$ and $B_0$ including means for recording a black body radiator at different temperatures and plotting the pixel intensity obtained versus a theoretically calculated intensity, and the axis intercept of a straight line, which is fitted to the data, for providing the individual zero level in each pixel of the images, consisting of self-radiation from the dual-image camera device;

means for calculating a gas correlation image, $G=(A-A_0)/(B-B_0)$;

means for calculating the concentration level in each pixel of image G arranged to use a diagram showing the integrated transmission within the chosen spectral profile as a function of the integrated concentration of the gas expressed in ppm× meter for the particular gas, temperature difference between the background temperature and the gas emission temperature, and absolute temperatures; and means for displaying the result by superimposing the resulting gas concentration image on a visible image C of the scene.

11. A device according to claim 10, characterised in that the display means is arranged to colour-code the gas concentration image.

12. A device according to claim 10 or 11, consisting of a reflector double telescope with two off-axis parabolas for simultaneous capturing of the images A and B, two plane and angled secondary mirrors designed to avoid the self-radiation of the infrared camera to be reflected back into the camera detector, and a camera, which is used to simultaneously capture the visible image C, mounted in close proximity to the telescope.

13. A device according to claim 10 or 11, consisting of two infrared micro-bolometer cameras mounted together for simultaneous capturing of the images A and B. The sensitivities of the infrared cameras are tuned to the selected wavelength region with the use of antireflection coatings and interference filters, and a camera, which is used to simultaneously capture the visible image C, mounted in close proximity to the infrared cameras.

14. A device according to claim 10 or 11, consisting of two infrared QWIP (Quantum Well Infrared Photodetector) cameras mounted together for simultaneous capturing of the images A and B with sensitivities of the detectors optimized for the selected wavelength region, and a camera, which is used to simultaneously capture the visible image C, mounted in close proximity to the infrared cameras.

15. A device according to claim 10 or 11, consisting of an infrared camera with two detectors capturing images A and B with the aid of a beam-splitter and gas correlation cell inside the camera, and a camera, which is used to simultaneously capture the visible image C, mounted in close proximity to the infrared camera.

16. A device according to claim 10 or 11, consisting of an infrared camera with one detector sequentially capturing images A and B by the use of a chopper switching the gas correlation cell in and out in front of the detector, and a camera, which is used to simultaneously capture the visible image C, mounted in close proximity to the infrared camera.

17. A gas correlation imaging device comprising:

at least one image detector oriented so as to record a plurality of infrared images of a gaseous region;

a gas correlation cell disposed relative to the at least one of the image detectors such that one of the plurality of images of the gaseous region passes through the gas correlation cell before being recorded by the at least one of the image detectors; and a computer linked to the at least one of the image detectors for processing each received image of the gaseous region with the computer configured to subtract an image offset from each one of the plurality of images that is based on a recorded background temperature.

18. A gas correlation imaging device according to claim 17 comprising a plurality of the image detectors with one of the image detectors spaced from the other one of the image detectors, and wherein (a) the gas correlation cell is disposed relative to one of the plurality of the image detectors such that one of the plurality of infrared images passes through the gas correlation cell before reaching the one of the plurality of image detectors, (b) a first infrared image of the plurality of infrared images comprised of a plurality pixels is received by one of the plurality of the image detectors without passing through the gas correlation cell and a second infrared image of the plurality of infrared images comprised of a plurality of pixels is received by the other one of the plurality of the image detectors after passing through the gas correlation cell, (c) the image offset is based on recording a black body radiator at different temperatures, and (d) the image offset is applied by the computer to each pixel of each one of the images.

19. A gas correlation imaging device according to claim 18 wherein the plurality of image detectors comprise a dual infrared camera device and further comprising a double telescope optical lens arrangement for directing one of the images onto one of the image detectors of the dual infrared camera device and the other one of the images onto the other one of the image detectors with the gas correlation cell disposed between the gaseous region and the other one of the image detectors of the dual infrared camera device.

20. A gas correlation imaging device according to claim 17 further comprising a visible image camera recording a visible image of the gaseous region and a linked to the computer that superimposes in real time on the visible image display color coded gas concentration image formed from the plurality of infrared images.

21. A method of imaging gaseous emissions comprising:

(a) providing at least one image detector oriented so as to record a plurality of infrared images of a gaseous region, a gas correlation cell disposed relative to the at least one of the image detectors such that at least one of the plurality of images of the gaseous region passes through the gas correlation cell before being recorded by the at least one of the image detectors, and a computer linked to the at least one image detector for processing the plurality of recorded infrared images;

(b) recording a first infrared image of the gaseous region without the image passing through the gas correlation cell before being recorded;

(c) recording a second infrared image of the gaseous region after the image has passed through the gas correlation cell;

(d) obtaining a temperature of a background;

(e) using the temperature of the background to obtain an image offset;

(f) determining a gas correlation image comprised of a plurality of pixels using the first infrared image, the second infrared image, and the offset; and (g) determining a gas concentration level for each pixel of the gas correlation image.

22. A method of imaging gaseous emissions according to claim 21 wherein before step (e) obtaining the image offset comprises obtaining a transmittance value using a temperature of the gaseous region to calculate a difference between the temperature of the background region and the temperature of the gaseous region, and thereafter using the calculated temperature difference to obtain a relative transmittance value from a function of relative transmittance versus temperature difference produced by recording a black body radiator at a plurality of temperatures, and wherein the obtained transmittance value is subtracted from the value of each pixel of the first and second infrared images.

23. A method of imaging gaseous emissions according to claim 21 wherein in step (e) the gas correlation image is the result of (1) subtracting the image offset from the first infrared image to produce a first result, (2) subtracting the image offset from the second infrared image to produce a second result, and thereafter (3) dividing the first result by the second result.

24. A method of imaging gaseous emissions according to claim 21 wherein before step (e) the step further comprising digitally overlapping the first infrared image and the second infrared image, and thereafter determining the gas correlation image and the gas concentration level only for an image field that defines gas in the gaseous region.

25. A method of imaging gaseous emissions according to claim 21 further comprising providing a visible image camera that simultaneously records a visible light image of the gaseous region during steps (b) and (c), and after step (g) the step further comprising assigning a color to each pixel of the gas correlation image based on the gas concentration level determined for that pixel in step (g) to create a colorized gas correlation image and thereafter displaying the colorized gas correlation image superimposed on the visible light image of the gaseous region in real time.

* * * * *

UNITED STATES PATENT AND TRADEMARK OFFICE
CERTIFICATE OF CORRECTION

PATENT NO. : 6,803,577 B2
DATED : October 12, 2004
INVENTOR(S) : Hans Edner, Jonas Sandsten and Sue Svanberg It is certified that error appears in the above-identified patent and that said Letters Patent is hereby corrected as shown below:

Column 5,
Lines 16-17, delete "or 2, characterized by the adaption of the infrared camera detector" and substitute -- further comprising adapting an --;
Line 18, delete "and" and substitute -- or --; after "threshold" insert -- of the infrared camera detector --;
Lines 22-23, delete "or 2, characterized by a determination of the" and substitute -- further comprising determining a --;
Line 24, delete "the" and substitute -- a --; after "velocity" delete the comma and insert -- that is --;
Line 25, delete "the gas" and substitute -- a --; after "cloud" insert -- of the gas --;
Lines 27-28, delete "or 2, characterized of the utilization of" and substitute -- further comprising utilizing --;
Line 29, delete "simultaneous" and substitute -- simultaneously --; delete "of the"; delete the period after "B";
Lines 30-31, delete "The visible image C is simultaneously captured with a camera mounted in close proximity to the telescope" and substitute -- and utilizing a second camera mounted in close proximity to the telescope for simultaneously capturing image C --;
Line 36-37, delete "or 2, characterized by the use of" and substitute -- wherein the dual image infrared camera device comprises --;
Line 38-39, delete the period after "B"; delete "The visible image C is simultaneously captured with a camera mounted in close proximity to the infrared cameras" and substitute -- and further comprising a third camera that is mounted in close proximity to the two infrared cameras for simultaneously capturing visible image C --;
Lines 41-42, delete "or 2, characterized by the use of" and substitute -- wherein the dual image infrared camera device comprises --;
Lines 44-46, delete the period after "camera" and insert a comma; delete "The visible image C is simultaneously captured with a camera mounted in close proximity to the infrared camera" and substitute -- and further comprising another camera mounted in close proximity to the infrared camera for simultaneously capturing visible image C --;
Lines 47-48, delete "or 2, characterized by the use of" and substitute -- comprising utilizing --;
Lines 50-53, after "detected" delete the period; delete "The visible image C is simultaneously captured with a camera mounted in close proximity to the infrared camera" and substitute -- and utilizing another camera mounted in close proximity to the infrared camera that simultaneously captures visible image C --;

UNITED STATES PATENT AND TRADEMARK OFFICE
CERTIFICATE OF CORRECTION

PATENT NO. : 6,803,577 B2
DATED : October 12, 2004
INVENTOR(S) : Hans Edner, Jonas Sandsten and Sue Svanberg It is certified that error appears in the above-identified patent and that said Letters Patent is hereby corrected as shown below:

Column 6,
Line 24, delete "or 11, consisting of" and substitute -- further comprising --;
Line 28, delete "to be" and substitute -- from being --;
Line 32, delete "or 11, consisting of" and substitute -- further comprising --;
Line 34, delete "the"; delete the period after "B" and substitute a comma; delete "The" and substitute -- with the --;
Line 35, delete "infrared" and substitute -- micro-bolometer --; delete "are" and substitute -- being --; delete "the" and substitute -- a --;
Line 36, after "of" insert -- an --; delete "coatings" and substitute -- coating --; after "and" insert -- an --;
Line 37, delete "filters" and substitute -- filter --; delete "a" and substitute -- another --;
Line 39, delete "infrared" substitute -- micro-bolometer --;
Line 40, "or 11, consisting of" and substitute -- further comprising --;
Line 41, delete "QWIP"; delete the parentheses before "Quantum" and after "Photodetctor";
Line 42, delete "the";
Line 43, after "B" insert a comma;
Line 44, delete "the" and substitute -- a --; delete "a" and substitute -- another --;
Line 46, after "infrared" insert -- Quantum Well Infrared Photodetector --;
Line 47, delete "or 11, consisting of" and substitute -- comprising --;
Line 50, delete "a" and substitute -- another --;
Line 53, delete "or 11, consisting of" and substitute -- comprising --;
Line 56, after "a" insert -- second --.

UNITED STATES PATENT AND TRADEMARK OFFICE
CERTIFICATE OF CORRECTION

PATENT NO. : 6,803,577 B2
DATED : October 12, 2004
INVENTOR(S) : Hans Edner, Jonas Sandsten and Sue Svanberg It is certified that error appears in the above-identified patent and that said Letters Patent is hereby corrected as shown below:

Column 7,
Line 34, after "a" insert -- display --.

Signed and Sealed this

Third Day of May, 2005

JON W. DUDAS
*Director of the United States Patent and Trademark Office*